United States Patent
Sisler et al.

(10) Patent No.: US 8,592,345 B2
(45) Date of Patent: Nov. 26, 2013

(54) METHODS OF INHIBITING ETHYLENE RESPONSES IN PLANTS USING DICYCLOPROPENE COMPOUNDS

(75) Inventors: Edward C. Sisler, Raleigh, NC (US); Varvara Grichko, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 1210 days.

(21) Appl. No.: 12/138,500

(22) Filed: Jun. 13, 2008

(65) Prior Publication Data
US 2009/0203801 A1 Aug. 13, 2009

Related U.S. Application Data

(60) Provisional application No. 60/945,782, filed on Jun. 22, 2007, provisional application No. 60/950,645, filed on Jul. 19, 2007.

(51) Int. Cl.
*A01N 27/00* (2006.01)
*C07C 13/04* (2006.01)

(52) U.S. Cl.
USPC ............ 504/357; 504/114; 504/189; 585/2

(58) Field of Classification Search
USPC ............ 585/16, 20, 23, 2; 504/114, 189, 357
See application file for complete search history.

(56) References Cited

U.S. PATENT DOCUMENTS

| | | | |
|---|---|---|---|
| 4,851,035 A | 7/1989 | Pirrung et al. | |
| 5,518,988 A * | 5/1996 | Sisler et al. | 504/114 |
| 6,194,350 B1 | 2/2001 | Sisler | |
| 6,365,549 B2 | 4/2002 | Sisler | |
| 6,426,319 B1 * | 7/2002 | Kostansek | 504/357 |
| 6,767,856 B1 * | 7/2004 | Crowther | 502/103 |
| 6,770,600 B1 * | 8/2004 | Lamola et al. | 504/357 |
| 2001/0019995 A1 * | 9/2001 | Sisler | 504/114 |

FOREIGN PATENT DOCUMENTS

WO WO 01/37663 5/2001

OTHER PUBLICATIONS

Schipperijn, et al., "Chemistry of Cyclopropene III. Synthesis of Mono- and Dialkylated Cyclopropenes" in Rec. Tray. Chim. Pays-Bas, 92, 1973, 1159-1166—1973, month unknown.*
Billups, et al., "Bicycloprop-2-enyl (C6H6)" in Angew. Chem. Int. Ed. Engl., 28 (1989), 1711-1712—1989, month unknown.*
Sauer, et al., "An One-Pot Synthesis of Semibullvalenes and its Mechanism" in Eur. J. Org. Chem., 2002, 791-801—2002, month unknown.*
Komatsu, et al., "Syntheses and Properties of the Polymethylenebis(diphenylcyclopropenium) Dications" in Bull. Chem. Soc. Jpn., 55(8), 2470-2479—1979, month unknown.*
Paske et al. "Eintopfsynthese füf substituierte Semibullvalene", *Angew. Chem.* 92(6):464-465 (1980).

(Continued)

*Primary Examiner* — In Suk Bullock
*Assistant Examiner* — Bradley Etherton
(74) *Attorney, Agent, or Firm* — Myers Bigel Sibley & Sajovec, P.A.

(57) ABSTRACT

Methods of applying dicyclopropene compounds and compositions thereof to block ethylene receptors in plants are disclosed. Methods include applying to the plant an effective ethylene response-inhibiting amount of a dicyclopropene compound or composition thereof. Dicyclopropene compounds, enantiomers, stereoisomers or salts thereof are also provided.

5 Claims, 1 Drawing Sheet

(56) References Cited

OTHER PUBLICATIONS

Billups et al. "Bicycloprop-2-enyl (C$_6$H$_6$)" *Angew. Chem.* 101(12):1735-1737 (1989).
Mango "The Role of Coordinate Bonding in Metal-Catalyzed Symmetry-Forbidden Valence Isomerizations", *Tetrandron Letters* 6:505-508 (1971).
Reisenauer et al. "Cyclopropenyliden", *Angew. Chem.* 96(8):596 (1984).
Davis et al. "Stereochemistry of the Cope Rearrangement and Mechanism of Thermal Aromatization of 3,3'-Bicyclopropenyls", *J. Am. Chem. Soc.* 99(5):1499-1507 (1977).
Sauer et al. "Database Beilstein (Online)", *Beilstein Institute for Organic Chemistry* 5:791-802 (2002).
Maier et al. "Hexa-tertbutyl-3,3'-bicyclopropenyl", *Chem. Ber.* 125:2111-2117 (1992).
Maier et al. "Database Beilstein (Online)", *Beilstein Institute for Organic Chemistry* 1:173-186 (1995), Abstract.
Ciabattoni et al. "Di-*t*-butylcyclopropenone and Substituted Di-*t*-butylcyclopropenyl Cations" *J. Am. Chem. Soc.* 91(17):4766-4771 (1969).
Schipperijn et al. "Chemistry of Cyclopropene III.: Synthesis of mono- and dialkylated cyclopropenes" *Recueil Des Traveaux Chimiques Des Pays-Bas.* 92:1159-1166 (1973).
Grayston et al. "Database Beilstein (Online)", *Beilstein Institute for Organic Chemistry* 98:1278-1280.
Breslow et al. "Database Beilstein (Online)", *Beilstein Institute for Organic Chemistry* 84:3168-3174.
Ivanov et al. "Database Beilstein (Online)", *Beilstein Institute for Organic Chemistry* 24(12):2298-2303 (1988).
Maier et al. "Database Beilstein (Online)", *Beilstein Institute for Organic Chemistry* 98(12):1132-1134 (1986).
Maier et al. "Database Beilstein (Online)" *Beilstein Institute for Organic Chemistry* 125(9):2111-2118 (1992).
Haley et al. "Database Beilstein (Online)", *Beilstein Institute for Orianic Chemistry* 36(20):3457-3460 (1995).
Streitwieser et al. "Inverse sandwich compounds", *Theochem* 40:259-265 (1988).
Minyaev "Theoretical study of the stability of semisandwich and sandwich organic structures with an axial AB group (A=carbon, nitrogen; B=oxygen, nitrogen, sulfur)", *Zhurnal Organicheskoi Khimii* 20(5):897-07 (1984).
Priyakumar et al. "Structure, stability and reactivity parameters of (CH)8 isomers and their cation and anion radical counterparts: A theoretical study", *Indian Journal of Chemistry, Section A: Inorganic, Bio-inorganic, Physical, Theoretical, & Analytical Chemistry* 39A(1-3):92-99 (2000).
Versteeg et al. "The valence isomers of (CH)8 and (SiH)8: an ab initio MO study", *J. Computational Chem.* 15(10):1151-1162 (1994).
Ilic et al. "On normalization of topological resonance energy", *Croatica Chemica Acta* 52(1):35-42 (1979).
Maier et al. "Small rings. 90. Peralkyl-substituted tetrahedranes", *Liebigs Annalen* 1:173-186 (1955).
Sauer et al. "An one-pot synthesis of semibullvalenes and its mechanism", *European J. Org. Chem.* 5:791-801 (2002).
Grueger et al. "3,3,',3'-Tetramethy1-2,2'-bis(trimethylsily1)-1,1'-bicyclopropenyksynthesis and isomerization", *Tetrahedron Letters* 27(14):1563-1564 (1986).
Grueger et al. "3,3,',3'-Tetramethy1-2,2'-bis(trimethylsilyI)-1,1'-bicyclopropenyl:synthesis and isomerization", *Tetrahedron Letters* 27(14):1563-1564 (1986).
Boger et al. "Dimethyl 1,2,4,5-Tetrazine-3,6-dicarboxylate", *e-Eros Encyclopedia of Reagents for Organic Synthesis* (2001)—no page number given.
Bochvar et al. "Molecular orbital calculations of 1,5-dicyclopropenylcyclooctatetraene", *Izvestiya Akademii Nauk SSSR, Seriya Khimicheskaya* 4:756-757 (1966).
Grichko "New Volatile and Water-Soluble Ethylene Antagonists" *Russian Journal of Plant Physiology* 53(4):523-529 (2006).
Notification of Transmittal of the International Search Report and the Written Opinion of the International Searching Authority, or the Declaration corresponding to International Application No. PCT/US08/007402 mailed Nov. 19, 2008.

\* cited by examiner

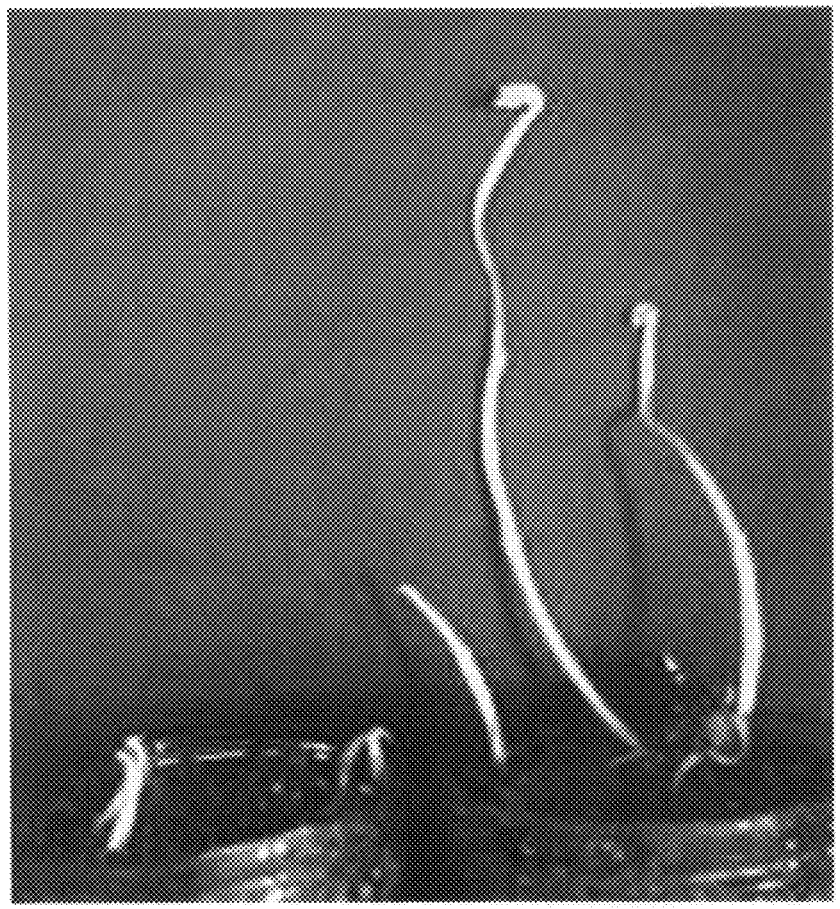

METHODS OF INHIBITING ETHYLENE RESPONSES IN PLANTS USING DICYCLOPROPENE COMPOUNDS

RELATED APPLICATION DATA

This application claims the benefit of U.S. Provisional Application Ser. No. 60/945,782, filed on Jun. 22, 2007, and U.S. Provisional Application Ser. No. 60/950,645, filed on Jul. 19, 2007. The disclosure of each application is incorporated by reference herein in its entirety.

STATEMENT OF GOVERNMENT SUPPORT

Aspects of this research are supported by the Binational Agricultural Research and Development Fund (BARD) under grant number US-IS-3493-02CR. The U.S. Government has certain rights to this invention.

FIELD OF THE INVENTION

The present invention generally relates to methods of blocking ethylene responses in plants and plant materials by applying dicyclopropene compounds and compositions thereof to plants. The invention further relates to dicyclopropene compounds, enantiomers, stereoisomers and salts thereof.

BACKGROUND OF THE INVENTION

Ethylene is known to mediate a variety of growth phenomena in plants. See generally Fritz et al. U.S. Pat. No. 3,879,188. This activity is understood to be achieved through a specific ethylene receptor in plants. Many compounds other than ethylene interact with this receptor: some mimic the action of ethylene; while others prevent ethylene from binding and thereby counteract its action.

Many compounds that block the action of ethylene do so by binding to the ethylene binding site. Unfortunately, they often diffuse from the binding site over a period of several hours. See E. Sisler and C. Wood, *Plant Growth Reg.* 7, 181-191 (1988). These blocking compounds may be used to counteract ethylene action. However, a problem with such compounds is that exposure must be continuous if the effect is to last for more than a few hours.

Photoaffinity labeling has been used in biological studies to label binding sites in a permanent manner—usually by generating a carbene or nitrene intermediate. Such intermediates are generally reactive and react rapidly and indiscriminately with many compositions. A compound already bound, however, would react mostly with the binding site. In a preliminary study, it was shown that cyclopentadiene was an effective blocking agent for ethylene binding. See E. Sisler et al., *Plant Growth Reg.* 9, 157-164 (1990). Methods of combating the ethylene response in plants with diazocyclopentadiene and derivatives thereof are described in U.S. Pat. No. 5,100,462 to Sisler et al. U.S. Pat. No. 5,518,988 to Sisler et al. describes the use of cyclopropenes having a $C_1$ to $C_4$ alkyl group to block the action of ethylene.

Notwithstanding these efforts, however, there remains a need in the art for additional methods providing improved plant maturation and degradation regulation as well as those for counteracting ethylene-induced processes in agricultural produce and/or horticultural products.

SUMMARY OF THE INVENTION

The present invention includes dicyclopropene compounds of Formula I:

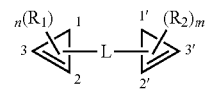

wherein:
m and n are independently an integer from 0 to 4;
$R_1$ and $R_2$ are independently $C_1$-$C_{20}$ alkyl, $C_2$-$C_{20}$ alkenyl or $C_2$-$C_{20}$ alkynyl, wherein at least one of $R_1$ or $R_2$ is $C_1$-$C_5$ alkyl, $C_2$-$C_5$ alkenyl, or $C_2$-$C_5$ alkynyl; and
L is selected from the group consisting of a covalent linkage, phosphorus, oxygen, sulfur, $C_1$-$C_{20}$ alkyl, $C_2$-$C_{20}$ alkenyl, $C_2$-$C_{20}$ alkynyl, $C_3$-$C_8$ cycloalkyl, heterocyclyl and aryl, or
an enantiomer, stereoisomer or a salt thereof.

In some embodiments, the compound has the following structure:

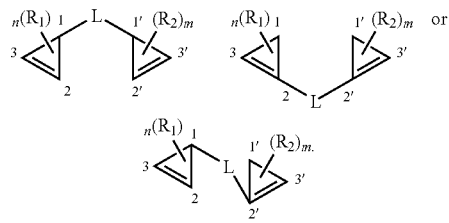

In particular embodiments, the compound has the following structure:

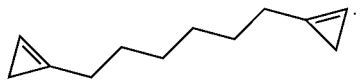

Embodiments of the present invention further provide compositions including: (a) at least one of a compound of Formula I; and (b) an adjuvant, such as an agriculturally acceptable carrier.

The present invention further includes methods of inhibiting ethylene responses in plants and plant materials. Methods include inhibiting an ethylene response in a plant, including applying to the plant an effective ethylene response-inhibiting amount of a compound of Formula I or a composition including at least one of a compound of Formula I; and (b) an adjuvant. In some embodiments, the compounds include those having the following structure:

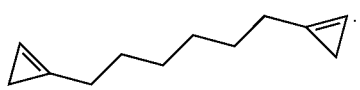 [SMILES: C1=C(CCCCCCC2=CC2)C1]

Application of the compounds to a plant may be carried out by contacting the plant to a gaseous or salt form of the compound or a mixture thereof, contacting the plant with a solid including the compound, applying a spray including the compound, dipping the plant in a composition including the compound, and addition of the compound to a container containing the plant. Additionally, compounds of the present invention can be applied in an open or closed system. In particular embodiments, compounds of the present invention can be used outside, for example, on field crops or landscape plants.

Embodiments of the present invention further provide methods of prolonging the life of a cut flower or fresh produce, including applying to the cut flower or fresh produce an effective life-prolonging amount of the dicyclopropene compounds described herein.

Aspects of the present invention may result in the prolongation of storability and shelf life of produce, such as fruits and vegetables, extension of the storage and vase life of cut flowers, extension of the harvest timing for field crops and/or prolongation of life of landscape plants.

According to further aspects of the present invention, the compounds described herein are useful to provide protection against ethylene regulated processes in vascular plants.

BRIEF DESCRIPTION OF THE DRAWINGS

FIG. 1. Effect of 1,6-dicyclopropenyl-hexane on etiolated plea plant growth.

DETAILED DESCRIPTION

Ethylene receptors are thought to form higher-order clusters composed of receptor dimer subunits. The receptor dimers can influence the signaling states of neighboring dimers through direct contact. Accordingly, transmitters from many receptors may be altered by a single ligand-binding event. Dicyclopropene compounds can be involved in cross-linking in ethylene receptor clusters. The compounds disclosed herein may exhibit significant anti-ethylene activity. In some embodiments, the compounds can be volatile, work efficiently at different temperatures, active at 0.3 nL L$^{-1}$ when applied as a gas and/or protect fruits from ethylene for up to about 42 days.

Unless otherwise defined, all technical and scientific terms used herein have the same meaning as commonly understood by one of ordinary skill in the art to which this invention belongs. Further, all publications, U.S. patent applications, U.S. patents and other references cited herein are incorporated by reference in their entireties.

The present invention can be practiced based upon the disclosure described herein, in light of the knowledge of persons skilled in the art, and in light of the information set forth in U.S. Pat. No. 6,365,549; U.S. Pat. No. 6,194,350; and U.S. Pat. No. 5,518,988. The disclosures of all of which are incorporated by reference herein in their entirety.

Dicyclopropene compounds that may be used to carry out the present invention may be prepared by using various methods known to those skilled in the art. For example, as described by Baird et al. in *Preparation and Lithiation of 1-Halogenocyclopropenes*, J. CHEM. SOC. PERKIN TRANS. I 1845-53 (1986). Additionally, dicyclopropenes can be prepared using methods described by N. I. Yakushkina and I. G. Bolesov in *Dehydrohalogenation of onohalogenocyclopropanes as a Method for the Synthesis of Sterically Screened Cyclopropenes*, RUSSIAN J. OF ORGANIC CHEM. 15:853-59 (1979).

Dicyclopropene compounds of the present invention include those of Formula

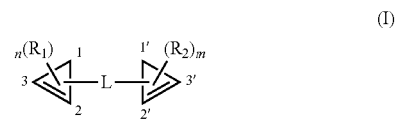

wherein:
m and n are independently an integer from 0 to 4. $R_1$ and $R_2$ are independently $C_1$-$C_{20}$ alkyl, $C_2$-$C_{20}$ alkenyl or $C_2$-$C_{20}$ alkynyl, wherein at least one of $R_1$ or $R_2$ is $C_1$-$C_5$ alkyl, $C_2$-$C_5$ alkenyl or $C_2$-$C_5$ alkynyl. L is selected from the group consisting of a covalent linkage, phosphorus, oxygen, sulfur, magnesium, $C_1$-$C_{20}$ alkyl, $C_2$-$C_{20}$ alkenyl, $C_2$-$C_{20}$ alkynyl, $C_3$-$C_8$ cycloalkyl, heterocyclyl and aryl. In some embodiments, n and m are independently 1 or 2. In other embodiments, n and m are each 0. In further embodiments, L is $C_1$-$C_6$, $C_6$, $C_1$-$C_{12}$, $C_{12}$, or $C_4$-$C_{10}$ alkyl, $C_4$-$C_8$ cycloalkyl or $C_3$-$C_8$ cycloalkyl. In further embodiments, at least one of $R_1$ or $R_2$ is an alkyl, alkenyl, or alkynyl substituted with at least one substituent selected from the group consisting of halogen, amino, alkoxy, carboxy, alkoxycarbonyl and hydroxy. In other embodiments, at least one of the carbon atoms in at least one of $R_1$ or $R_2$ is replaced by at least one substituent selected from the group consisting of an ester, nitrile, amine, amine salt, acid, acid salt, an ester of an acid, hydroxy, and a heteroatom selected from the group consisting of oxygen and nitrogen. In some embodiments, at least one of $R_1$ or $R_2$ is hexyl, and in other embodiments, at least one of $R_1$ or $R_2$ is octyl.

According to aspects of the present invention, one end of L may attach to any one of position 1, 2 or 3 and the opposite end of L may attach to any position of 1',2' or 3'. In particular embodiments, the compound has the following structure:

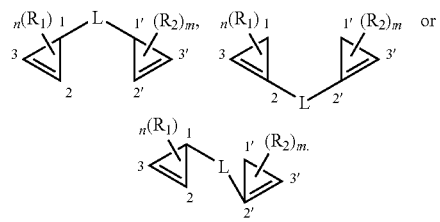

According to embodiments of the present invention, the compound is 1,6-dicyclopropenyl-hexane. In particular embodiments, the compound has the following structure:

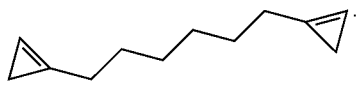

Embodiments of the present invention further include enantiomers, stereoisomers and salts of the dicyclopropene compounds described herein.

The terms "alkyl", "alkenyl", and "alkynyl", as used herein, refer to linear or branched alkyl, alkenyl or alkynyl substituents, which may be unsubstituted or substituted. Moreover, a range, such as $C_1$-$C_6$, means that the carbon chain can be $C_1$, $C_2$, $C_3$, $C_4$, $C_5$, or $C_6$ or any range inclusive of any of the values included in the range, for example, $C_2$-$C_4$. As used herein, the term "heterocyclyl", heterocycle" or "heterocyclic" refer to saturated or partially unsaturated monocyclic, bicyclic or tricyclic groups having from 3 to 15 atoms, in some instances 3 to 7, with at least one heteroatom in at least one of the rings. As used herein, "aryl" refers to an aromatic group in a single or fused carbocyclic ring system having from 6 to 15 ring atoms, in some instances 6 to 10, and includes substituted aromatic groups. Examples of aryl groups include, but are not limited to, phenyl, 1-naphthyl, 2-naphthyl and benzyl. As used herein, the term "halogen", "halo" or "halide" refers to fluoro, fluorine or fluoride, chloro, chlorine or chloride, bromo, bromine or bromide, and iodo, iodine or iodide, accordingly.

Embodiments of the present invention further include a composition comprising, consisting essentially of or consisting of (a) at least one of a compound of Formula I:

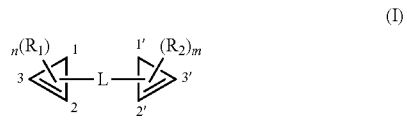

(I)

wherein m and n are independently an integer from 0 to 4; $R_1$ and $R_2$ are independently $C_1$-$C_{20}$ alkyl, $C_2$-$C_{20}$ alkenyl or $C_2$-$C_{20}$ alkynyl, wherein at least one of $R_1$ or $R_2$ is an unsubstituted or substituted $C_1$-$C_5$ alkyl, $C_2$-$C_5$ alkenyl, or $C_2$-$C_5$ alkynyl; L is selected from the group consisting of a covalent linkage, phosphorus, oxygen, sulfur, magnesium, $C_1$-$C_{20}$ alkyl, $C_2$-$C_{20}$ alkenyl, $C_2$-$C_{20}$ alkynyl, $C_3$-$C_8$ cycloalkyl, heterocyclyl and aryl, or an enantiomer, stereoisomer or a salt thereof; and (b) an acceptable adjuvant such as an agriculturally acceptable carrier.

Agricultural compositions including the dicyclopropene compounds described herein are also encompassed by the invention. In some embodiments, the compositions include 0.005% to 99%, by weight; in other embodiments 1% to 95%, by weight; in further embodiments 2% to 90%, by weight; in still further embodiments 3% to 80%, by weight; and in some embodiments, 4% to 70%, by weight, of the active compounds of the present invention. As used herein, all percentages are percent by weight and all parts are parts by weight, unless otherwise specified, and are inclusive and combinable. All ratios are by weight and all ratio ranges are inclusive and combinable. All molar ranges are inclusive and combinable.

These compositions may include one or more adjuvants, such as, for example, carriers, extenders, binders, lubricants, surfactants and/or dispersants, wetting agents, spreading agents, dispersing agents, stickers, adhesives, defoamers, thickeners, and emulsifying agents. Such adjuvants commonly used in the art can be found in the John W. McCutcheon, Inc. publication Detergents and Emulsifiers, Annual, Allured Publishing Company, Ridgewood, N.J., U.S.A. The term "agriculturally acceptable carrier" refers to adjuvants that are ordinarily used in agricultural formulation technology.

Numerous organic solvents may be used as carriers for the active compounds of the present invention, e.g., hydrocarbons such as hexane, benzene, toluene, xylene, kerosene, diesel oil, fuel oil and petroleum naphtha, ketones such as acetone, methyl ethyl ketone and cyclohexanone, chlorinated hydrocarbons such as carbon tetrachloride, esters such as ethyl acetate, amyl acetate and butyl acetate, ethers, e.g., ethylene glycol monomethyl ether and diethylene glycol monomethyl ether, alcohols, e.g., ethanol, methanol, isopropanol, amyl alcohol, ethylene glycol, propylene glycol, butyl carbitol acetate and glycerine.

Mixtures of water and organic solvents, either as solutions or emulsions, can also be employed as inert carriers for the active compounds.

The active compounds of the present invention may also include adjuvants or carriers such as talc, pyrophyllite, synthetic fine silica, attapulgus clay (attaclay), kieselguhr, chalk, diatomaceous earth, lime, calcium carbonate, bentonite, fuller's earth, cottonseed hulls, wheat flour, soybean flour pumice, tripoli, wood flour, walnut shell flour, redwood flour and lignin.

It may be desirable to incorporate a wetting agent in the compositions of the present invention. Such wetting agents may be employed in both the solid and liquid compositions. The wetting agent can be anionic, cationic or nonionic in character.

Typical classes of wetting agents include alkyl sulfonate salts, alkylaryl sulfonate salts, alkyl sulfate salts, alkylamide sulfonate salts, alkylaryl polyether alcohols, fatty acid esters of polyhydric alcohols and the alkylene oxide addition products of such esters, and addition products of long chain mercaptans and alkylene oxides. Typical examples of such wetting agents include the sodium alkylbenzene sulfonates having 10 to 18 carbon atoms in the alkyl group, alkylphenol ethylene oxide condensation products, e.g., p-isooctylphenol condensed with 10 ethylene oxide units, soaps, e.g., sodium stearate and potassium oleate, sodium salt of propylnaphthalene sulfonic acid (di-2-ethylhexyl), ester of sodium sulfosuccinic acid, sodium lauryl sulfate, sodium stearate and potassium oleate, sodium salt of the sulfonated monoglyceride of coconut fatty acids, sorbitan, sesquioleate, lauryl trimethyl ammonium chloride, octadecyl trimethyl ammonium chloride, polyethylene glycol lauryl ether, polyethylene esters of fatty acids and rosin acids (e.g., Ethofat® 7 and 13, commercially available from Akzo Nobel Chemicals, Inc. of Chicago, Ill.), sodium N-methyl-N-oleyltaurate, Turkey Red oil, sodium dibutylnaphthalene sulfonate, sodium lignin sulfonate (Maraspersee® N, commercially available from LignoTech USA of Rothschild, Wis.), polyethylene glycol stearate, sodium dodecylbenzene sulfonate, tertiary dodecyl polyethylene glycol thioether, long chain ethylene oxide-propylene oxide condensation products (e.g., Pluronice 61 (molecular weight 1,000) commercially available from BASF of Mount Olive, N.J.), sorbitan sesquioleate, polyethylene glycol ester of tall oil acids, sodium octyl phenoxyethoxyethyl sulfate, polyoxyethylene (20) sorbitan monolaurate (Tween® 20, commercially available from ICI Americas Inc. of Wilmington, Del.) tris (polyoxyethylene) sorbitan monostearate (Tween® 60, commercially available from ICI Americas Inc. of Wilmington, Del.), and sodium dihexyl sulfosuccinate. Solid, liquid, and gaseous formulations can be prepared by various conventional procedures. Thus, the active ingredient, in finely divided form if a solid, may be tumbled together with finely divided solid carrier. Alternatively, the active ingredient in liquid form, including mixtures, solutions, dispersions, emulsions and suspensions thereof, may be admixed with a solid carrier in finely divided form. Furthermore, the active ingredient in solid form may be admixed with a liquid carrier to form a mixture, solution, dispersion, emulsion, suspension or the like.

Embodiments of the present invention further include methods of inhibiting an ethylene response in a plant, comprising, consisting essentially of or consisting of applying to the plant an effective ethylene response-inhibiting amount of at least one compound of Formula I:

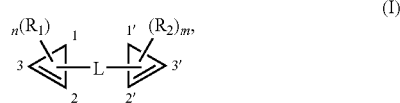

wherein m and n are independently an integer from 0 to 4; $R_1$ and $R_2$ are independently $C_1$-$C_{20}$ alkyl, $C_2$-$C_{20}$ alkenyl or $C_2$-$C_{20}$ alkynyl, wherein at least one of $R_1$ or $R_2$ is $C_1$-$C_5$ alkyl, $C_2$-$C_5$ alkenyl or $C_2$-$C_5$ alkynyl; and L is selected from the group consisting of a covalent linkage, phosphorus, oxygen, sulfur, magnesium, $C_1$-$C_{20}$ alkyl, $C_2$-$C_{20}$ alkenyl, $C_2$-$C_{20}$ alkynyl, $C_3$-$C_8$ cycloalkyl, heterocyclyl and aryl, or an enantiomer, stereoisomer or a salt thereof.

In particular embodiments, the compound has the following structure:

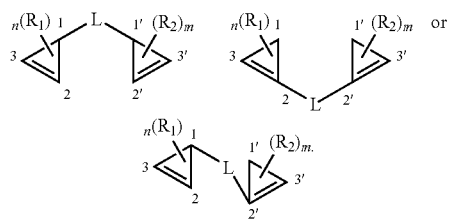

The active compounds of the present invention can be applied to plants by various suitable means. For example, an active compound may be applied alone in gaseous, liquid, or solid form or a mixture of any combination thereof by contacting the compound with the plant to be treated. Additionally, the active compound may be converted to the salt form, and then applied to the plants. Alternatively, compositions containing one or more active compounds of the present invention may be formed. The compositions may be applied in gaseous, liquid, or solid form or a mixture of any combination thereof by contacting the composition with the plant to be treated. Such compositions may include an inert carrier. Suitable solid carriers include dusts. Similarly, when in gaseous form, the compound may be dispersed in an inert gaseous carrier to provide a gaseous solution. The active compound may also be suspended in a liquid solution such as an organic solvent or an aqueous solution that may serve as the inert carrier. Solutions containing the active compound may be heterogeneous or homogeneous and may be of various forms including mixtures, dispersions, emulsions, suspensions and the like.

The active compounds and compositions thereof can also be applied as aerosols, e.g., by dispersing them in air using a compressed gas such as, for example, nitrogen, carbon dioxide, dichlorodifluoromethane, trichlorofluoromethane, or other halocarbons.

Accordingly, in some embodiments, methods of the present invention can be carried out by contacting a plant to a gaseous form of a dicyclopropene compound described herein, spraying a plant with a solution including the dicyclopropene compounds described herein and/or contacting a plant to a solid including the dicyclopropene compounds described herein.

The present invention can be employed to modify a variety of different ethylene responses. Ethylene responses may be initiated by either exogenous or endogenous sources of ethylene. Ethylene responses include, for example, the ripening and/or senescence of flowers, fruits and vegetables, abscission of foliage, flowers and fruit, the shortening of the life of ornamentals such as potted plants, cut flowers, shrubbery, and dormant seedlings, in some plants (e.g., pea) the inhibition of growth, and in other plants (e.g., rice) the stimulation of growth. Additional ethylene responses or ethylene-type responses that may be inhibited by active compounds of the present invention include, but are not limited to, auxin activity, inhibition of terminal growth, control of apical dominance, increase in branching, increase in tillering, changing biochemical compositions of plants (such as increasing leaf area relative to stem area), abortion or inhibition of flowering and seed development, lodging effects, stimulation of seed germination and breaking of dormancy, and hormone or epinasty effects. Thus, in some embodiments, the dicyclopropene compounds described herein inhibit one or more of ripening or senescence of flowers, fruits, and vegetables; abscission of foliage, flowers, and fruit; the shortening of life of ornamental plants, cut flowers, shrubbery, seeds, or dormant seedlings; inhibition of growth; stimulation of growth; auxin activity; inhibition of terminal growth; control of apical dominance; increase in branching; increase in tillering; changing the morphology of plants; modifying the susceptibility to plant pathogens such as fungi; changing biochemical compositions; inducing pest resistance; abortion or inhibition of flowering or seed development; lodging effects; stimulation of seed germination; breaking of dormancy; hormone effects; and epinasty effects. In some embodiments, the plant is a whole plant and or any portions thereof, a field crop, landscape plant, potted plant, cut flower, or harvested fruit or vegetable.

In some embodiments the ethylene response is fruit ripening, vegetable ripening, and/or flower senescence.

In some embodiments, the compounds can be applied in a closed or open system. In some embodiments, the compounds can be used as a gas in a closed system, for example, indoors or applied to a plant in a container or in a greenhouse. In other embodiments, the compounds can be used a salt, which can be used, for example, in a spray, in an open system, such as outdoors, for example, on field crops or landscape plants including flowers.

The term "plant" is used in a generic sense herein, and includes woody-stemmed plants such as trees and shrubs. Plants to be treated by the methods described herein include whole plants and any portions thereof, field crops, landscape plants, potted plants, cut flowers (stems and flowers), and harvested fruits and vegetables. Accordingly, plants include agricultural produce, such as fresh produce, and landscape plants such as trees, shrubs, potted plants and ornamental plants.

Plants treated with the compounds or compositions and by the methods of the present invention are preferably treated with a non-phytotoxic amount of the active compound.

Vegetables that may be treated by the method of the present invention to inhibit an ethylene response, such as ripening and/or senescence, include leafy green vegetables such as lettuce (e.g., *Lactuea sativa*), spinach (*Spinaca oleracea*), and cabbage (*Brassica oleracea*), various roots, such as potatoes (*Solanum tuberosum*) and carrots (*Daucus*), bulbs, such as onions (*Allium* sp.), herbs, such as basil (*Ocimum basilicum*), oregano (*Origanum vulgare*), dill (*Anethum graveolens*), as well as soybean (*Glycine max*), lima beans (*Phaseolus limensis*), peas (*Lathyrus* spp.), corn (*Zea mays*), broccoli (*Brassica oleracea* italica), cauliflower (*Brassica oleracea* botrytis), and asparagus (*Asparagus officinalis*).

Fruits which may be treated by the method of the present invention to inhibit an ethylene response, such as ripening, include tomatoes (*Lycopersicon esculentum*), apples (*Malus* domestica), bananas (*Musa sapientum*), pears (*Pyrus communis*), papaya (*Carica papaya*), mangoes (*Mangifera indica*), peaches (*Prunus persica*), apricots (*Prunus armeniaca*), nectarines (*Prunus persica* nectarina), oranges (*Citrus* sp.), lemons (*Citrus limonia*), limes (*Citrus aurantifolia*), grapefruit (*Citrus paradisi*), tangerines (*Citrus nobilis* deliciosa), kiwi (*Actinidia chinenus*), melons such as cantaloupe (*C. cantalupensis*) and musk melon (*C. melo*), pineapple (*Aranas comosus*), persimmon (*Diospyros* sp.), various small fruits including berries such as strawberries (*Fragaria*), blueberries (*Vaccinium* sp.) and raspberries (e.g., *Rubus ursinus*), green beans (*Phaseolus vulgaris*), members of the genus *Cucumis* such as cucumber (*C. sativus*), and avocados (*Persea americana*).

Ornamental plants that may be treated by the method of the present invention to inhibit an ethylene response, such as senescence and/or shortening of flower life and, thus prolong flower life and appearance (e.g., delay wilting), include potted ornamentals, and cut flowers. Potted ornamentals and cut flowers which may be treated with the present invention include azalea (*Rhododendron* spp.), hydrangea (*Macrophylla hydrangea*), hybiscus (*Hibiscus rosasanensis*), snapdragons (*Antirrhinum* sp.), poinsettia (*Euphorbia pulcherima*), cactus (e.g. *Cactaceae schlumbergera* truncata), begonias (*Begonia* sp.), roses (*Rosa* spp.), tulips (*Tulipa* sp.), daffodils (*Narcissus* spp.), dandelions (*Taraxacum offinale*), petunias (*Petunia hybrida*), carnation (*Dianthus caryophyllus*), lily (e.g., *Lilium* sp.), gladiolus (*Gladiolus* sp.), alstroemeria (*Alstoemeria brasiliensis*), anemone (e.g., *Anemone blanda*), columbine (*Aquilegia* sp.), aralia (e.g., *Aralia chinensis*), aster (e.g., *Aster carolinianus*), bougainvillea (*Bougainvillea* sp.), camellia (*Camellia* sp.), bellflower (*Campanula* sp.), cockscomb (*celosia* sp.), falsecypress (*Chamaecyparis* sp.), chrysanthemum (*Chrysanthemum* sp.), clematis (*Clematis* sp.), cyclamen (*Cyclamen* sp.), freesia (e.g., *Freesia refracta*), and orchids of the family Orchidaceae.

Plants which may be treated by the method of the present invention to inhibit an ethylene response, such as abscission of foliage, flowers and fruit, include cotton (*Gossypium* spp.), apples, pears, cherries (*Prunus avium*), pecans (*Carva illinoensis*), grapes (*Vitis vinifera*), olives (e.g. *Vitis vinifera* and *Olea europaea*), coffee (*Coffea arabica*), snapbeans (*Phaseolus vulgaris*), and weeping fig (*Ficus benjamina*), as well as dormant seedlings such as various fruit trees including apple, ornamental plants, shrubbery, and tree seedlings. In addition, shrubbery which may be treated according to the present invention to inhibit an ethylene response, such as abscission of foliage, include privet (*Ligustrum* sp.), photinea (*Photinia* sp.), holly (*Ilex* sp.), ferns of the family Polypodiaceae, schefflera (*Schefflera* sp.), aglaonema (*Aglaonema* sp.), cotoneaster (*Cotoneaster* sp.), barberry (*Berberis* sp.), waxmyrtle (*Myrica* sp.), abelia (*Abelia* sp.), acacia (*Acacia* sp.) and bromeliades of the family Bromeliaceae.

Field crops which may be treated by the methods of the present invention include a plurality of, or at least more than one, tree, bush, shrub, plant, etc. including the vegetables, fruits, ornamental plants and plants discussed herein.

Active compounds of the present invention have proven to be unexpectedly potent inhibitors of ethylene action on plants, fruits and vegetables, even when applied at low concentrations and varying temperatures. Among other things, compounds of the present invention may result in a longer period of insensitivity to ethylene than compounds found in the prior art. This longer period of insensitivity may occur even when compounds of the present invention are applied at a lower concentration than previous compounds, at varying temperatures and/or when applied as a gas or spray.

The present invention is explained in greater detail in the following non-limiting examples. In these examples, µl means microliters; ml means milliliters; nl means nanoliters; l means liters; cm means centimeters; and temperatures are given in degrees Celsius.

Example 1

General Procedure of the Preparation of Dicyclopropene Compounds

The dicyclopropene compounds can be prepared by using a modified procedure of Al Dulayymi et al. (1996 and 1997). All appropriate starting materials are either commercially available or can be readily prepared by one of ordinary skill in the art. The appropriate starting material can react with bromoform in the presence of 50% NaOH and subsequently react with methyllithium to provide the desired dicyclopropene compounds. (See Al Dulayymi J. R., et al., Structure based interference with insect behaviour-Cyclopropenes analogs of pheromones containing Z-Alkenes, *Tetrahedron,* 52, 12509-12520 (1996); Al Dulayymi A. R., et al., Simple four and five carbon cyclopropane and cyclopropene synthetic intermediates, Russian. *J. Org. Chem.,* 33, 798-816 (1997); Al Dulayymi J. R., et al., Synthesis of Putative ~6-, 12 and ~15-Desaturase Inhibitors, *Tetrahedron,* 53, 1099-1110 (1997)).

Example 2

Preparation of 1,6-dicyclopropenyl-hexane 1,9-Decadiyne (CAS Registry Number: 1720-38-3) was used as a starting material, and it was brominated to provide the intermediate 2,9-dibromodeca-1,9-diene by using the procedure of Couseau, J, *Synthesis,* 805-806 (1980). Then the 2,9-dibromodeca-1,9-diene reacted with bromoform and NaOH and subsequently reacted with methyllithium to provide 1,6-dicylcopropenyl-hexane by using the procedure of Dulayymi, J R et al. *Tetrahedron,* 53, 1099-1110 (1997) and Dulayymi, J R et al. *Tetrahedron,* 52, 12509-12520, (1996).

Example 3

Effect of 1,6-dicyclopropenyl-hexane on Pea Plant Growth 1,6-dicyclopropenyl-hexane was synthesized and found to exhibit significant anti-ethylene activity as shown in FIG. 1. FIG. 1 (left) shows pea plants grown in the presence of 1 ppm of ethylene. FIG. 1 (right) shows pea plants grown in the presence of both 1 ppm of ethylene and 1,6-dicyclopropenyl-hexane. 1,6-dicyclopropenyl-hexane was shown to be volatile, work efficiently at different temperatures, active at 0.3 nL $L^{-1}$ when applied as a gas and/or protect bananas from ethylene responses for at least about 42 days.

The foregoing embodiments and examples are illustrative of the present invention and are not to be construed as limiting thereof. The invention is defined by the following claims, with equivalents of the claims to be included therein.

That which is claimed is:

1. A composition comprising:

(a) a compound having the following structure:

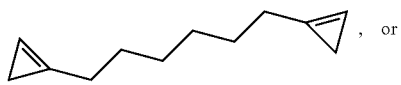 [SMILES: C1=C(CCCCCCC2=CC2)C1], or an enantiomer, stereoisomer or a salt thereof; and
(b) an agriculturally acceptable carrier.

2. The composition of claim 1, wherein the compound is in a salt form.

3. The composition of claim 1, wherein the composition is in a solid form.

4. The composition of claim 1, wherein the composition is in a liquid form.

5. The composition of claim 1, wherein the composition is in a gaseous form.

* * * * *

UNITED STATES PATENT AND TRADEMARK OFFICE
CERTIFICATE OF CORRECTION

| | | |
|---|---|---|
| PATENT NO. | : 8,592,345 B2 | Page 1 of 1 |
| APPLICATION NO. | : 12/138500 | |
| DATED | : November 26, 2013 | |
| INVENTOR(S) | : Sisler et al. | |

It is certified that error appears in the above-identified patent and that said Letters Patent is hereby corrected as shown below:

On Title Page:
Page 2, References Cited, Other Publications, left column, "Grayston et al."
    Correct "1278-1280."
    to read -- 1278-1280 (1976). --

Page 2, References Cited, Other Publications, left column, "Breslow et al."
    Correct "3168-3174."
    to read -- 3168-3174 (1962). --

In the Specifications:
Column 3, Line 67: Correct "include those of Formula"
              to read -- include those of Formula I: --

Signed and Sealed this
Sixth Day of May, 2014

Michelle K. Lee
*Deputy Director of the United States Patent and Trademark Office*